United States Patent [19]

Shoyab et al.

[11] Patent Number: 4,714,683

[45] Date of Patent: Dec. 22, 1987

[54] POLYPEPTIDE TUMOR INHIBITORS AND ANTIBODIES THERETO

[75] Inventors: Mohammed Shoyab, Seattle; Hans Marquardt, Mercer Island; George J. Todaro, Seattle, all of Wash.

[73] Assignee: Oncogen, Seattle, Wash.

[21] Appl. No.: 694,712

[22] Filed: Jan. 25, 1985

[51] Int. Cl.$^4$ .................. G01N 33/53; G01N 33/534; G01N 33/577; G01N 33/68
[52] U.S. Cl. .................................... 436/547; 436/548; 436/804; 530/300; 530/324; 530/326; 530/328; 530/329; 530/330; 530/350; 530/387
[58] Field of Search ........ 260/112 R, 112 B, 112.5 R; 436/501, 548, 547; 536/26, 27, 28, 29; 530/300, 328, 329, 330, 350, 324, 326, 387

[56] References Cited

U.S. PATENT DOCUMENTS

| | | | |
|---|---|---|---|
| 4,428,875 | 1/1984 | De Barbieri | 530/331 |
| 4,457,867 | 7/1984 | Ishida | 530/351 X |
| 4,529,594 | 7/1985 | Hayashi | 514/12 |

OTHER PUBLICATIONS

Guidotti, A. et al., Nature, 275 (5680), 553–555 (Oct. 12, 1978).
Chemical Abstracts, I, 94:76605m (1981).
Chemical Abstracts, II, 98:83311z (1983).

Primary Examiner—Sidney Marantz
Attorney, Agent, or Firm—Bertram I. Rowland

[57] ABSTRACT

Polypeptides, polynucleotide sequences, DNA constructs and compositions are provided for the preparation and use of polypeptides associated with naturally occurring polypeptides found in brains. The small molecular weight polypeptides are growth inhibitors for neoplastic cells without inhibiting normal cells. The polypeptides comprise specific regions which are highly conserved, separated by less conserved regions. The polypeptides find use in inhibiting neoplastic growth and detecting receptors for the polypeptides. Antibodies are provided in conjunction with the polypeptides, which may be used together or separately for detecting the presence of the neoplastic cell retarding polypeptides.

18 Claims, No Drawings

POLYPEPTIDE TUMOR INHIBITORS AND ANTIBODIES THERETO

BACKGROUND OF THE INVENTION

1. Field of the Invention

Cellular growth and differentiation appear to be initiated, promoted, maintained and regulated by a multiplicity of stimulatory, inhibitory and synergistic hormones and factors. The alteration and/or breakdown of the cellular homeostasis mechanism seems to be a basic cause of growth related diseases including neoplasia. There is a considerable interest in the isolation, characterization and mechanism of action of growth modulatory factors (stimulators and inhibitors) because of their potential use in the diagnosis, prognosis and therapy of various diseases, such as cancer, as well as in understanding the basic mechanisms of mitosis, particularly as it may effect cancer.

The detection, isolation and purification of these factors is frequently complicated by the complexity of the mixture, the divergencies of activities of the various components in the mixtures, the sensitivity of components to deactivation by a wide variety of reagents, the potential for having compounds which depend for their activity on the presence of multiple subunits, and the frequent difficulties in providing bioassays for tracking various purification steps. Nevertheless, there have been substantial advances in purification and separation, which advances have aided in the detection and isolation of products of interest.

2. Description of the Prior Art

Beal et al., *Cancer Biochem. Biophys.* (1979) 3: 93–96 report the presence of peptides in human urine which inhibit growth and DNA synthesis more in transformed cells than in normal cells. Holley et al., *Proc. Natl. Acad. Sci.* (1980) 77: 5989–5992 describe the purification of epithelial cell growth inhibitors. Letansky, *Biosci. Rep.* (1982) 2: 39–45 report that peptides purified from bovine placenta inhibit tumor growth and thymidine incorporation in DNA to a greater extent in neoplasms than in normal cells. Chen, *Trends Biochem. Sci.* (1982) 7: 364–365 reports the isolating of a peptide from ascites fluid with a cancer suppressing property. Redding and Schally, *Proc. Natl. Acad. Sci.* (1982) 79: 7014–7018 report isolation of purified peptide(s) from porcine hypothalmi which exhibit antimitogenic activity against several normal and tumor cell lines. Most of these factors have not been fully characterized, nor are their primary structures known.

SUMMARY OF THE INVENTION

Novel methods and compositions are provided for preparing novel polypeptides having neoplastic cell growth retarding activity, while not retarding normal cell growth activity. The polypeptides are small, have amino acid sequences common with or the same as polypeptides found in mammalian brains and may be used by themselves or in conjunction with other compounds for tumor cell growth inhibition. Polynucleotide sequences are provided encoding the polypeptides, which allow for production of the polypeptides in prokaryotes or eukaryotes. Antibodies are provided which bind specifically to the subject polypeptides.

DESCRIPTION OF THE SPECIFIC EMBODIMENTS

Novel polymeric compounds are provided, which are poly(amino acids) or polynucleotides encoding for the poly(amino acids). The poly(amino acids) have a substantially greater growth retarding effect on neoplastic cell growth than any retarding effect on normal cell growth. The polypeptides have common amino acid sequences with polypeptides found in mammalian brains. The polypeptides are characterized by being of less than about 20 kilodaltons (kDal), usually less than about 15 kDal and will usually be at least about 2 kDal, more usually at least about 5 kDal.

The polypeptide compositions are further characterized by eluting from a $\mu$-Bondapak-$C_{18}$ column in reverse phase HPLC under ambient conditions employing a linear gradient of 0–60% acetonitrile in 0.1% aqueous trifluoroacetic acid in the range of 30–50% acetonitrile, particularly 30–40% acetonitrile, and more particularly about 33–36% acetonitrile.

With lung carcinoma cells, such as A549, 50% growth inhibition can be achieved with less than about 1 $\mu$g/ml, usually less than about 0.5 $\mu$g/ml and as low as 0.1 $\mu$g/ml or lower, usually requiring at least about 50 ng/ml. The conditions for the test are described in the Experimental section, and include a medium of DMEM and 10% FCS, at 37° C. The subject compositions are similarly effective in inhibiting soft agar colony formation and plating efficiency as described in the Experimental section.

The polypeptides will have at least about 15 amino acids, more usually at least about 20 amino acids, and fewer than about 125 amino acids, usually fewer than about 100 amino acids. The naturally occurring compounds will have a molecular weight in the range of about 8 to 18 kDal using PAGE or gel permeation chromatography as described in the Experimental section.

The polypeptide composition will be further characterized by having at least one of the following amino acid sequences, preferably at least two of the following amino acid sequences, and more preferably at least three of the following amino acid sequences, where the sequence may be conserved by the insertion or deletion of up to and including three amino acids or combination thereof.

| | |
|---|---|
| Yaa$^e$aa$^a$YKQATaa$^b$ | a. |
| KWDAW | b. |
| AMaa$^c$AY(X)$_x$VEE | c. |
| TKPaa$^d$aa$_p$EEMLFIYaa$^e$HYK | d. | wherein:

aa$^a$ is an aromatic amino acid, particularly phenylalanine and histidine;

aa$^b$ is any amino acid, particularly an aliphatic amino acid, which may be acidic, basic, or neutral, preferably acidic or neutral of from about 3 to 5 carbon atoms;

aa$^c$ may be any amino acid, particularly an aliphatic amino acid, which is basic, acidic or neutral, more particularly basic or neutral of from about 5 to 6 carbon atoms;

$aa^d$ is an aliphatic neutral amino acid, which may be polar or non-polar, particularly having an hydroxyl substituent and of from about 3 to 4 carbon atoms;

$aa^e$ is an aliphatic neutral amino acid, which may be polar or non-polar, particularly having an hydroxyl substituent and of from about 2 to 4 carbon atoms;

$aa^p$ is an aliphatic amino acid which may be neutral polar or acidic, particularly acidic or the amide thereof, and of from 4 to 5 carbon atoms;

X is from 1 to 3 amino acids, which may be any amino acids, particularly aliphatic amino acids, more particularly having a first neutral amino acid, a second acidic amino acid or amide thereof, and a third basic amino acid;

x is 0 or 1.

For the purposes of the subject invention, the various amino acids will be divided into a number of subclasses. The following Table indicates the subclasses:

| aliphatic | | | | | |
|---|---|---|---|---|---|
| neutral | | | | | |
| non-polar | G | A | P | V | L | I |
| polar | S | T | C | M | N | Q |
| acidic | D | E | | | | |
| basic | K | R | | | | |
| aromatic | F | H | Y | W | | |

Of particular interest are polypeptides having the above physiological characteristics and including at least one of the following amino acid sequences:

TKPaa$^d$DEEMLFIYaa$^e$HYKQATaa$^f$G  a.

KWDAWaa$^g$aa$^h$Laa$^i$aa$^j$aa$^k$aa$^l$K-Eaa$^m$AMaa$^n$AY(X)$_x$VEEaa$^o$KK  b.

wherein:

$aa^d$ and $aa^e$ are as defined previously;

$aa^f$ is an aliphatic amino acid, which may be neutral or acidic, particularly of from about 4 to 6, more particularly of from 5 to 6 carbon atoms;

$aa^g$ is an aliphatic neutral amino acid, particularly a polar amino acid of from about 3 to 5, more usually of from 3 to 4 carbon atoms, particularly having an hydroxyl or carboxamido polar substituent;

$aa^h$ is an aliphatic amino acid, which may be neutral or acidic, particularly polar or acidic, having an hydroxyl substituent and of from about 3 to 5 carbon atoms;

$aa^i$ is an aliphatic amino acid, particularly a neutral or basic amino acid, more particularly a non-polar neutral amino acid, of from about 2 to 6 carbon atoms;

$aa^j$ is an aliphatic amino acid, either neutral or acidic, when neutral, preferably non-polar, and particularly of from about 2 to 5, more usually of from 2 to 4 carbon atoms;

$aa^k$ is an aliphatic neutral amino acid, particularly a polar amino acid of from about 3 to 5, more usually of from 4 to 5 carbon atoms, having a chalcogen (oxygen or sulfur) functionality, particularly hydroxyl or methylthio;

$aa^l$ is an aliphatic neutral amino acid, particularly a polar amino acid, having an hydroxyl functionality and of from about 3 to 4 carbon atoms;

$aa^m$ is an aliphatic acidic amino acid of from 4 to 5 carbon atoms;

$aa^n$ is an aliphatic neutral or basic amino acid, of from about 3 to 6, particularly of from 4 to 6 carbon atoms, where the aliphatic neutral amino acid is preferably non-polar;

X' is the same as X, usually from 1 to 3 amino acids which are aliphatic amino acids, which may be neutral, acidic or basic, generally of from 4 to 6 carbon atoms, particularly in the order in the N—C direction neutral non-polar, acidic or amide thereof, and basic;

x is 0 or 1;

$aa^o$ is an aliphatic neutral amino acid, which may be polar or non-polar, particularly of from about 4 to 6, usually 5 to 6 carbon atoms, when polar, particularly having a methylthio group.

It being understood, that besides the X, there may be from 1 to 3, preferably 1 to 2, insertions or deletions to maintain the consensus structure between the various members of the family of polypeptides of this invention. Also, the amino acids are the naturally-occurring L-amino acids, although in some instances the D-amino acid may find use.

Compounds of particular interest have the following formula:

$\phi$-$Z^N$-$aa^1$-$aa^2$-$aa^3$-$aa^4$-$aa^5$-$aa^6$-$aa^7$-$aa^8$-K-$aa^{10}$-$aa^{11}$-$aa^{12}$ $aa^{13}$-$aa^{14}$-P-$aa^{16}$-$aa^{17}$-E-$aa^{19}$-M-L-$aa^{22}$-$aa^{23}$-Y-S $aa^{26}$-Y-K-Q-A-T-$aa^{32}$-G-$aa^{34}$-$aa^{35}$-$aa^{36}$-$aa^{37}$-$aa^{38}$ $aa^{39}$-P-G-$aa^{42}$$aa^{43}$-D-$aa^{45}$-$aa^{46}$-G-$aa^{48}$-$aa^{49}$-K-W-D A-W-$aa^{55}$-$aa^{56}$-L-$aa^{58}$-$aa^{59}$-$aa^{60}$-$aa^{61}$-K-E-$aa^{64}$-A M-$aa^{67}$-A-Y-$(X)_x$-V-E-E-$aa^{73}$-K-K-$aa^{76}$-$aa^{77}$-$aa^{78}$ $aa^{79}$-$Z^c$ wherein:

$\phi$ is H or acetyl;

$Z^N$ is a bond or from 1 to 10 amino acids, preferably from 1 to 9 amino acids, which may be aliphatic or aromatic, where the sequence is selected from the sequence $$V-H-E-T-R-\genfrac{}{}{0pt}{}{F}{S}-\genfrac{}{}{0pt}{}{E}{Q}-A-\genfrac{}{}{0pt}{}{A}{E},$$

so that any sequence of amino acids within such sequence may be joined to $aa^1$, for example E-A-A or H-E-T-R, or the like, where one may select either amino acid where two amino acids appear at the same site, preferably the amino acids on the same line being taken together;

$aa^{4,8,11}$ are aliphatic neutral non-polar amino acids of from 2 to 6 carbon atoms, particularly glycine, alanine, proline, valine, leucine and isoleucine;

$aa^{5,16,25,35,37,55,60,61,73,79}$ are aliphatic neutral non-polar or polar amino acids, where particularly $aa^{5,16,25,35,37,73,79}$ are either, while the remainder are preferably polar amino acids, particularly serine, threonine, cysteine, methionine, asparagine and glutamine;

$aa^{1,6,7,17,19,32,34,38,56,59,64,78}$ are aliphatic neutral amino acids, including polar and non-polar amino acids or aliphatic acidic amino acids, i.e., aspartic and glutamic amino acids; particularly, $aa^{1,7,32,34,59,78}$ are non-polar when neutral amino acids with the remainder being polar when neutral amino acids, and $aa^{1,6,7,17,19,34,38,56,64}$ are preferably acidic amino acids;

$aa^{2,10,13,23,26,42,43,45,49,77}$ are aliphatic neutral amino acids or aromatic amino acids, particularly phenylalanine, histidine, tyrosine and tryptophan, preferably aa$^{2,10,26,45,77}$ are preferably aromatic amino acids, while the remaining amino acids are preferably aliphatic amino acids;

aa$^{3,9,12,14,36,39,46,48,58,67,76}$ are aliphatic neutral or basic amino acids, i.e., lysine and arginine, where aa$^{3,58,67,76}$ are preferably non-polar when other than basic and the remainder are preferably polar when other than basic, except for aa$^{46}$ which may be either polar or non-polar, and aa$^{3,12,14,46,48,58,67,76}$ are preferably basic amino acids;

aa$^{22}$ is basic or aromatic, particularly phenylalanine;

X and x have been defined previously;

Z$^C$ is OH, NH$^2$, or a sequence of from 1 to 6, usually 1 to 4 amino acids, particularly aliphatic amino acids of from 2 to 6, usually of from 4 to 6 amino acids, particularly polar or non-polar amino acids, particularly a sequence within the sequence M-P-M-T.

It is understood that one or more of the consensus amino acids may be changed, usually not involving more than two changes, and the consensus sequence may require the insertion or deletion of up to 3, preferably not more than 2, amino acids other than indicated as X.

Polypeptides of interest will have at least 15, preferably at least 30 amino acids in a sequence included in the following sequence:

```
F—E—A—A—V—K—V—I —Q—S—L—P—K—N—G—
S  Q   E F D K A A E E V K H L
           E                 R

—S—F—Q—P—T—N—E—M—M—L—K—F—Y—S —
 K T K   A D   E         F I   S
             S                 G

—F—Y—K—Q—A—T—E—G—P—C—K—L—S—K—
 H             V   D I N T E R

—P—G—F —W—D—P—V—G—R—Y—K—W—D—A—
    M L     F K     K A
                    T

—W—S—S—L—G—D—M—T—K—E—E—A—M—I —
  N E     K G T S     D     K

A—Y—*—*—*—V—E—E—M—K—K—I —L—E—T
    I D K         L       K Y G I
    N
``` wherein any amino acid at any site may be substituted for any other amino acid at that site, preferably amino acids above as taken together, while amino acids below are taken together, more preferably amino acids on the same line are taken together, and an asterisk (*) intends a bond (no amino acid at that site). The sequence may extended by up to a total of 10, usually up to a total of 8, amino acids, where the N-terminus may have the additional sequence V-H-E-T-R or any portion thereof and the C-terminus may have the sequence M-P-M-T, or any portion thereof.

Polypeptides of particular interest include polypeptides having at least about 15, preferably at least about 20, more preferably at least about 30 amino acids, included in one of the following sequences, where such sequences include at least 10, preferably at least 12, and more preferably at least 15 of the amino acids indicated with an asterisk (*).

```
              *
V—H—E—T—R—F—E—A—A—V—K—V—I—Q—S—
```

```
       20          *   *     *
—L—P—K—N—G—S—F—Q—P—T—N—E—M—M—

*        *     * * *       *
—L—K—F—Y—S—F—Y—K—Q—A—T—E—G—P—

* *           *         *
—C—K—L—S—K—P—G—F—W—D—P—V—G—R—

60 * *          *           *
—Y—K—W—D—A—W—S—S—L—G—D—M—T—K—

*  *  *     *   *  *     *  *
—E—E—A—M—I—A—Y—V—E—E—M—K—K—I—

—L—E—T—M—P—M—T
                                  (bBF)
 *
S—Q—A—E—F—D—K—A—A—E—E—V—K—H—L—

* 20     *    * *       *
—K—T—K—P—A—D—E—E—M—L—F—I—Y—S—

* * * *  *       *        40
—H—Y—K—Q—A—T—V—G—D—I—N—T—E—R—

* *    *      *     * * *  *
—P—G—M—L—D—F—K—G—K—A—K—W—D—A—

*    60 *          *  * *  *
—W—N—E—L—K—G—T—S—K—E—D—A—M—K—

* *         * * * 80 * *
—A—Y—I—D—K—V—E—E—L—K—K—K—Y—G—I

*                                (hBF)
S—Q—A—E—F—E—K—A—A—E—E—V—R—H—L—

* 20    *    * *       *
 K—T—K—P—S—D—E—E—M—L—F—I—Y—G—

* * * *  *        *        40
—H—Y—K—Q—A—T—V—G—D—I—N—T—E—R—

* *     *      *     * * * *
—P—G—M—L—D—F—T—G—K—A—K—W—D—A—

*    60 *          *  * *   *
—W—N—E—L—K—G—T—S—K—E—D—A—M—K—

* *         * * * 80 * *
—A—Y—I—N—K—V—E—E—L—K—K—K—Y—G—I
```

For particularly preferred compositions of the subject invention, the above sequences may not be changed by having more than about 5 amino acids, inserted, deleted, or substituted, or combinations thereof, preferably not more than about 3 amino acids.

The subject polypeptides may be used as antigens for the production of antibodies, which in turn may be used as antigens for the production of anti-idiotypic antibodies. Either polyclonal or monoclonal antibodies may be prepared in accordance with conventional ways. The subject polypeptides or fragments thereof, generally fragments having at least about 15 amino acids, may be used by themselves, but are preferably bound or linked to an adjuvant or antigen which activates the immune system. Various antigens may be used, such as serum albumins, keyhole limpet hemocyanin, globulins, or the like. A wide variety of techniques are available for linking to polypeptides, such as glutaraldehyde, maleimidobenzoic acid, diazobenzoic acid, or the like. Adjuvants include Freund's adjuvant, aluminum hydroxide, or the like. The antigen is injected into an appropriate host in conventional amounts, where one or more booster injections may be made in from 2 to 4 week intervals. Where monoclonal antibodies are employed, normally a mouse is injected with the original and booster injections and the spleen isolated and the splenocytes fused with an appropriate fusion partner in accordance with conventional techniques. See, for example, Galfre et al., *Nature* (1977) 266:550; Kennett et al., *Current Topics in Microbiology and Immunology* (1978) 81:77; U.S. Pat. Nos. 4,381,282 and 4,363,799. However, for special purposes, other mammals may be employed, such as primates, e.g., humans, for production of antibodies having human $F_c$ chains.

The polypeptides and antibodies which bind specifically to the subject polypeptides may find use individually or together, both in vivo and in vitro. Because of the tumor-inhibiting property of the polypeptides, the polypeptides may be used with mixtures of cells, including both normal and tumorigenic cells, to inhibit the overgrowth of the tumorigenic cells. The subject compounds can therefore be employed in such situations as when mutagenizing normal cells, where one wishes to distinguish between the differences occurring with normal cells and tumorigenic cells as a result of mutagenesis; inhibiting growth of tumorigenic cells where bone marrow has been removed from a mammalian host; detecting binding sits for the subject polypeptides in a cell population; and the like.

The polypeptides may be used by themselves or in combination with the antibodies in diagnosis for the polypeptides. Either or both may be labeled or unlabeled for use in diagnostic assays. A large number of diagnostic assays are described in the literature and include the binding, either directly or indirectly, to the subject polypeptides or antibodies of a variety of labels, such as enzymes, radionuclides, fluorescers, substrates, coenzymes, particles, e.g., magnetic particles, or the like. As illustrative of these assays, see for example, U.S. Pat. Nos. 3,817,837; 3,850,752; 4,174,384; 4,277,437 and 4,374,925.

Various assays are divided arbitrarily into homogeneous and heterogeneous immunoassays, where the distinction is based on whether the complex between the polypeptide and its antibody must be separated from the uncomplexed members of the specific binding pair. Various assays are referred to as EIA, ELISA, RIA, homogeneous EIA, dot-blot, Westerns, or the like.

The subject polypeptides may be used in vivo for inhibiting tumor cell growth, by injection into tumors, encapsulation into liposomes, where the liposomes may be bound to antibodies specific for or preferential for tumor cells, or the like.

Antibodies to the subject polypeptides may be used in themselves as antigens to produce anti-idiotypes, which may serve as competitive antigens, having epitopic sites competitive with epitopic sites of the subject polypeptides. These anti-idiotypes may therefore serve as tumor inhibitors as substitutes for the subject polypeptides or as antagonists for the subject polypeptides.

The subject polypeptides form a family of naturally occurring polypeptides which may be derived from natural sources, as well as non-naturally occurring polypeptides which share physiological properties, such as binding specificity and tumor cell inhibition. The naturally occurring compounds may be obtained from naturally occurring sources, primarily brain tissue. To isolate the subject compounds, brain tissue is freed of blood clots, homogenized, extracted with an organic solvent under acidic conditions (pH<4) and then dialyzed to remove low molecular weight material, that is material less than about 4 kDal. The resulting product is then freed of compounds which apparently act as inhibitors of its activity using a gel permeation column and an aqueous 0.1% trifluoracetic acid solution containing from about 35 to 45% acetonitrile elutant. The resulting fraction is further purified employing a reverse phase high pressure liquid chromatographic column, for example, a $\mu$-Bondapak-C18 column employing linear gradients of acetonitrile of from about 0 to 60% in aqueous 0.1% trifluoroacetic acid. The subject compounds are found in the fractions of from about 30 to 50% acetonitrile, more particularly from 30 to 40% acetonitrile.

Alternatively, the subject polypeptides may be synthesized in accordance with known techniques, particularly where the polypeptides are fewer than 30 amino acids, more particularly fewer than 25 amino acids. See, for example, Barany and Merrifield, *Solid-Phase Peptide Synthesis*, "The Peptides, Analysis Synthesis Biology," Special Methods in Peptide Synthesis, Part A, Vol. 2, Gross and Merenhofer, eds., Academic Press, N.Y. 1980, pp. 1–284.

For relatively large polypeptides, particularly those of about 20 amino acids or greater, more particularly of about 30 amino acids, hybrid DNA technology may be employed for obtaining sequences encoding for the polypeptide, which may then be used for expression of the desired polypeptide in accordance with known ways. Genomic DNA, cDNA, synthetic DNA or combinations thereof may be employed for coding for the polypeptides, the presence of any introns being accommodated by employing a host cell having a functioning splicing system for the introns. For the most part, an open reading frame will be employed (free of introns), where the sequence coding for the open reading frame will be joined to transcriptional and translational regulatory signals which are functional in the expression host.

The sequence provided in the experimental section, or fragments thereof, fragments having at least about 45 bases (15 codons or greater) may be employed for expression of polypeptides of the subject invention. By employing in vitro mutagenesis, mutagenesis, adaptors or the like, the sequences can be varied from the naturally-occurring sequence to produce sequences having silent mutations or codons that code for non-wild type amino acids. Thus, one can produce both naturally-occurring polypeptides and polypeptides having analogous physiological properties but differing is one or more amino acids.

The coding sequence which is employed may have blunt or cohesive ends for joining to other sequences. For expression, a large number of expression vectors are either commercially available or have been described in the literature. Thus, one can introduce the subject sequence into an expression vector for expression in an appropriate host. The hosts may be prokaryotic or eukaryotic, that is, bacteria, algae, fungi, e.g., yeasts, mammalian cells, e.g., mouse cells, hamster cells, monkey cells, or the like. The expression vector, whether completely assembled for insertion of the coding sequence or assembled in conjunction with the coding sequence for a polypeptide of the subject invention, will be characterized for the most part as follows. Usually, but not always, a replication system will be available, providing for a low or high copy number of an episomal element to be maintained in the host. Where integration of the coding sequence into the host genome is desired, the replication system will not be required. The coding sequence will be flanked at the 5' and 3' ends by transcriptional and translational initiation and termination regulatory signals respectively. Therefore, promoter regions will be employed at the 5' end, which may include capping sequences, operators for regulated expression, the absence of promoter regulation for constitutive expression, enhancer sequences, and the like. At the 3' terminus will be a terminator, stop codons, optimally a polyadenylation sequence, and the like. The expression construct of the transriptional and translational regulatory sequences and coding sequence will frequently be joined to one or more markers which allow for selection both as to the transformed hosts into which the vector has been introduced and providing for a competitive advantage for those cells which retain the expression vector. Markers may include complementation by providing prototrophy to an auxotrophic host, biocide resistance, such as resistance to various antibiotics, heavy metals, or the like, immunity, etc. The various sequences will be selected so as to be functional in the host.

With many expression vectors, a polylinker is present between the transcriptional and translational initiation and termination regulatory sequences which provide for a plurality of restriction sites. Thus, by appropriate design of the coding sequence or the use of adaptors, the coding sequence may be inserted into the polylinker region.

In certain situations, it may be desirable to join the coding sequence to a 5'-coding sequence so as to obtain a fused product, where the 5'-sequence codes for a leader sequence, particularly for a secretory leader sequence and processing signal. Various secretory leaders have been described in the literature; see, for example, U.S. Pat. No. 4,411,994, EPA Nos. 88,632 and 116,201. The coding sequence is joined in proper reading frame to the secretory leader and processing signal, whereby the fused coding sequence may then be inserted into the expression vector to provide for the expression construct.

Where the polypeptide is retained intracellularly, after growing the cells, the cells may be harvested and lysed and the polypeptide isolated. Where the polypeptide is secreted, the nutrient medium may be continuously exchanged and the polypeptide isolated. Various techniques exist for isolation and purification of polypeptides, such as affinity chromatography, HPLC, electrophoresis, gradient centrifugation, solvent extraction, and the like.

Depending upon the use, the subject compounds may be formulated in a variety of ways. For in vivo administration, the subject compounds may be introduced into a physiologically acceptable carrier, such as sterile water, saline, phosphate-buffered saline, ethanol, etc. The concentrations will vary widely depending upon the particular application, whether the application is localized or general, or the like. Administration may be parenterally, intravenously, intraperitoneally, intra-arterially, subcutaneously, etc.

The following examples are offered by way of illustration and not by way of limitation.

EXPERIMENTAL

Materials and Methods

Purification of Oncoretardine from Bovine Brain Acid-ethanol Extraction

Fresh bovine brain (440 g wet weight) was washed with cold phosphate buffered saline (PBS) to remove residual blood clots, and minced. The minced tissue was suspended in 2400 ml of extraction buffer consisting of 2379 ml ethanol (98%), 18.5 ml concentrated HCl, 84 mg phenylmethylsulfonyl fluoride and 2.5 ml of aprotinin (23 TIU/ml from bovine lung (Sigma Chemical Co.)]. The mixture was homogenized in a Waring commercial blender. The mixture was stirred at 4° C. overnight, centrifuged at 8,000 rpm in a Beckman type 19 rotor for 30 min, and the supernatant carefully removed (2066 ml). Chloroform (2066 ml) and 207 ml of acidified water (203 ml water and 4.0 ml concentrated HCl) was added to the supernatant, the mixture stirred vigorously for approximately an hour, and allowed to stand at room temperature to separate into two phases. The upper aqueous phase was carefully removed and dialyzed against 20 liters×2 changes of 0.1M acetic acid at 4° C. in a Spectrapor dialysis membrane tubing (cut-off 3,500MW) (American Scientific Products). The dialyzed supernatant was lyophilized. The lyophilized material (1.35 g) was termed crude fraction.

Gel Permeation Chromatography

A TSK-250 column (Bio-Rad) was attached to a high pressure liquid chromatography (HPLC) system. The crude fraction (8.0 mg/ml) was dissolved in 40% acetonitrile in 0.1% trifluoroacetic acid. A 0.25 to 0.75 ml aliquot (2–6 mg protein) of this mixture was injected and elution was performed isocratically with a mobile phase of 40% acetonitrile in 0.1% trifluoroacetic acid (TFA). The flow rate was 0.5 ml/min and chart speed was set at 0.5 cm/min. The chromatography was performed at room temperature. Fractions were collected, lyophilized and assayed in triplicate for growth inhibitory activity.

Once the position of the biologically active peak was determined, a few hundred chromatographic runs as described above were made. The active fractions for all runs were pooled and lyophilized. About 635 mg active material was obtained. This was called the TSK-250 fraction.

Reverse Phase High Pressure Liquid Chromatography (HPLC) of TSK-250 Fraction TSK-250 fraction was dissolved (2.5 mg/ml) in 0.1% TFA. This material (0.25–0.5 ml) was injected. The separation was carried out using a $\mu$-Bonapak-$C_{18}$ column (3.9 mm i.d.×30 cm) at room temperature. The flow rate was set at 1.0 ml/min and the chart speed was 0.5 cm/min. Linear gradients were used between the primary solvent 0.1% TFA and the secondary solvent acetonitrile in 0.1% TFA. The gradient conditions were 0–30% in 10 min., then 30–60% in one hour. All solvents were HPLC grade. Fractions were collected. Aliquots of each fraction were lyophilized and assayed in triplicate for growth inhibitory activity. Three active fractions termed $C_{18}$-A, B and C were observed which eluted at 34, 35 and 45% acetonitrile concentration respectively. Again, a few hundred chromatographic runs were made as above. The active fractions A, B and C from different runs were pooled separately and lyophilized.

Pooled fraction A from 10 runs was lyophilized and suspended in 0.225 ml of 0.1% TFA and rerun on the same column. The gradient conditions were 0–33% in 10 min, then 33–43% in 30 min. Aliquots of each fraction were lyophilized and tested for growth inhibitory activity. Most of the activity appeared in a single fraction corresponding to the major absorbance peak. Rechromatography of this fraction (2 runs) gave a single absorbance peak containing all the activity. About 650 $\mu$g of pure protein was obtained from 440 g of beef brain.

Purification of Oncoretardine from Human Brain

The human equivalent of bBF protein was purified to homogeneity from human brain employing the same methods as used for the isolation of bBF.

Cell Growth Modulatory Assay Using $^{125}$I-Deoxyuridine Incorporation into DNA The assays were performed in Nunc 96 well plates (Kamstrupvej 90. DK-4,000, Roskilde, Denmark). Human lung carcinoma cells (A549) were used as test cells. $3.5 \times 10^3$ cells in 50 $\mu$l of Dulbecco's modified Eagle's medium (DMEM) with 10% fetal calf serum (FCS) and penicillin/streptomycin (P/S) (0.57 mg/ml each) and glutamine were introduced to all wells except peripheral wells. The peripheral wells received 50 $\mu$l PBS and the plates were incubated at 37° C. The test samples were suspended in DMEM with 10% FCS, P/S, and glutamine for triplicate testing. After 4 hours, 50 $\mu$l of test samples were added to each test well, while control wells received only 50 $\mu$l of medium. Plates were incubated at 37° C. for 3 days. On day 4, 100 $\mu$l of a solution of $^{125}$I-iodo-2'-deoxyuridine [(4Ci/mg-0.5 mCi/ml) (1.0 $\mu$l isotope/ml in DMEM containing 10% FCS, P/S, glutamine)] were added to each well and plates incubated at 37° C. On day 5, the medium was aspirated from the wells, washed $1 \times$ with 200 $\mu$l PBS. Then, 200 $\mu$l methanol was added to each well, plates were incubated for 10 minutes and methanol removed by aspiration. Sodium hydroxide (200 $\mu$l, 1M) was added to each well, the plates were incubated for 30 min. at 37° C. and then sodium hydroxide removed with Titertek plugs (Flow Labs). The plugs were transferred into $12 \times 75$ mm plastic tubes and counted in a gamma counter in order to quantitate the radioactivity.

Soft Agar Colony Inhibition Assay

A 2.0 ml base layer of 0.5% agar (Agar Noble; Difco Laboratories, Detroit, Mich.) in DMEM containing 10% calf serum was added to 60 mm Costar tissue culture dishes. A 2.0 ml overlay of 0.3% agar containing the same medium-calf serum mixture, $1.0 \times 10^4$ A549 Ag3 (soft agar growing clone 3) cells and the sample to be tested at various concentrations in duplicate were added. The plates were incubated at 37° C. in a humidified atmosphere of 5% $CO_2$ in air and refed after 7 days by addition of 2.0 ml of 0.3% agar containing appropriate supplements. Colonies were measured unfixed, unstained and the number of colonies greater than 6 cells per 5 low power random fields were scored after 7 and 14 days.

Plating Efficiency Assay

The assay was performed in a 6 well Falcon plates (9.6 cm$^2$ area/well). A549 cells (200) were plated in each well in 1 ml of DMEM with 10% FCS, P/S and glutamine. Immediately following plating, various concentrations of test material in 1.0 ml of medium in duplicate were added to wells. The control wells received only 1.0 ml of medium without any test material. Plates were incubated at 37° C. in a humidified atmosphere of 5% $CO_2$ in air for 10 days, medium aspirated, 1.0 ml of 0.2% methylene blue in 50% methanol was added at each well and allowed to stand for 20 min., stain removed, each well washed $2 \times$ with 1.0 ml water and air dried. The size and number of colonies were quantitated.

Cell Growth Inhibitory Assay

A549 cells were plated at $2.1 \times 10^4$ cells per well in 0.3 ml medium (DMEM with 10% FCS, P/S, glutamine) in 24 well Costar plates (area—2 cm$^2$/well) and incubated for 2 hours at 37° C. Then, test samples at various concentrations in duplicate in 0.3 ml medium were introduced to each well. The control wells received only medium without any sample. Plates were incubated at 37° C. for 72 hours. The medium was then aspirated, the cells washed with 1.0 ml PBS/well, detached with 0.5 ml of trypsin (0.05%)-EDTA (0.5 mM) and counted using a Coulter counter.

Polyacrylamide Gel Electrophoresis (PAGE)

A 15 cm resolving gel (0.75 mm thick) of 15.6% polyacrylamide bis-acrylamide (30: 0.8) containing 0.1M sodium phosphate, pH7.2, 0.1% SDS and 6M urea was used. The gel contained 10 $\mu$l TEMED (Bio-Rad) per 20 ml of gel and was polymerized by using 1.0 $\mu$l/ml gel of 20% ammonium persulfate. An upper gel of a 3.5% acrylamide solution using buffer conditions identical to those of resolving gel was poured on top of the lower gel. The comb was inserted into the top gel, leaving about 3 mm of upper gel. 40 $\mu$l of samples in 0.01M sodium phosphate pH 7.2, 7M urea, 1% SDS and 1% 2-mercaptoethanol, was boiled for 2 minutes and quickly applied. The running buffer was 0.1M sodium phosphate, pH 7.2 containing 0.1% SDS. The gel was run at 5 volts/cm at room temperature until tracking dye reached the bottom of the gel. The gel was fixed in 50% methanol and 9% acetic acid, stained with 0.1% Coomasie blue in the fixing solution, and destained with 50% methanol and 9% acetic acid. Following destaining, the gel was dried.

The PAGE method of Laemmli, Nature (1970) 227: 680–685 was also used employing 15% resolving and 5% stacking gels.

Sequencing

The amino acid sequences of bovine and human brain factor were determined by microsequence analysis of peptides obtained from digests of bBF and hBF with (a) the endoproteinase Lysine C; (b) chymotrypsin; (c) Staphylococcal aureus V8; and (d) cyanogen bromide. The peptide fragments were purified by reverse phase HPLC using volatile solvents. Amino terminally blocked peptides were incubated in 12N HCl at ambient temperature for 16 hr. Samples were then dried by lyophilization. The peptides were subjected to automated repetitive Edman degradation in the Model 470A gas phase Protein Sequencer (Applied Biosystems). The phenylthiohydantoin amino acids were analyzed by reverse phase HPLC.

Purification of bBF from Human Brain

The human equivalent of bBF protein was purified to homogeneity from human brain employing the same method as used for the isolation of bBF.

Structural Homology Between Bovine and Human Brain Factor

Bovine brain factor (bBF) (300 pmol) and 600 pmol of human brain factor (hBF) were digested in 40 μl of 0.1M Tris-acetic acid buffer (pH 8.0) with the endoproteinase Lys-C (Boehringer) for 16 h at 24° C., respectively. The digestion was stopped by adding trifluoroacetic acid (50 μl). The Lys-C fragments were separated by rpHPLC on a μ Bondapak-C18 column (Waters) using a linear 2 h gradient from 0.05% trifluoroacetic acid in water to 60% acetonitrile containing 0.045% trifluoroacetic acid. The column eluate was continuously monitored by UV absorption at 214 nm.

RESULTS

Purification of Bovine Brain Oncoretardine (bBF)

A summary of the purification is presented in Table I.

TABLE I

Purification of Bovine Brain Oncoretardine

| Fraction | Weight (mg) | Units[a] | Specific activity (units/mg) | Yield (%) |
|---|---|---|---|---|
| Crude | 1,350[b] | 13,776 | 10.2 | 100 |
| TSK-250 | 635[b,c] | 30,238 | 47.6 | 219 |
| HPLC-C$_{18}$ | 0.651[c] | 6,853 | 10,526.8 | 42 |

[a]Material needed for 50% inhibition of $^{125}$I-deoxyuridine incorporation into DNA of A549 cells.
[b]Pooled material weighed directly.
[c]Calculated from absorption at 280 mμ of pooled material.

A 1032-fold purification with 42% yield was achieved. Reverse phase HPLC is the most crucial step in bBF purification. Total activity increased following TSK-250 chromatography over the previous step. Probably, an inhibitor(s) or antagonist(s) of bBF is separated from bBF during the TSK-250 step.

The homogeneity of the purified factor was demonstrated by PAGE in the presence of 6M urea. The molecular weight of the peptide was estimated to be 10.5 kDal by PAGE using ovalbumin (43K), carbonic anhydrase (30K), chymotrypsin inhibitor (21K), ribonuclease A (13.7K), aprotinin (6.6K) and insulin subunit (3K) as standards. The purified bBF emerged as a single symmetrical peak from Bio-Sil TSK-250 column (60 cm×7.5 mm 2.d) using 40% acetonitrile in 0.1% TFA as eluting solvent. The apparent molecular weight was calculated to be about 15 kDal by this gel permeation chromatography method.

Biological Properties

A 50% inhibition of DNA synthesis was observed at 98 μg/ml, 21 μg/ml and 95 ng/ml of crude fraction, TSK-250 fraction and the final pure protein, respectively. Thus, a 50% DNA synthesis inhibition in A549 human lung carcinoma cell was seen at approximately 9 nM concentration of the pure protein.

bBF also inhibited the anchorage independent growth of human carcinoma lung cells A549 on agar (Ag). A 50% reduction in colony formation in soft agar was seen at about 76 ng/ml of bBF. The plating efficiency of A549 cells were markedly inhibited by the protein. At 13 ng/ml (1.24 nM) concentration of protein, the plating efficiency was only 50% compared to that of the control. No colonies of A549 cells were seen in the presence of approximately 80 ng/ml bBF.

When A549 cells were grown in the absence and presence of various concentrations of bBF, and cell growth monitored by direct cell count, it was found that bBF inhibited cell growth in a dose dependent manner. Thus, the extent of $^{125}$I-deoxyuridine incorporation into DNA is a good measure of cell growth.

bBF inhibited the growth of various clones of A549 cells, human melanoma cells (A375 Ag) and human breast carcinoma cells (MCF-7). The growth of human foreskin fibroblast (WI-26) was stimulated by bBF. The brain factor was also growth stimulatory to murine fibroblastic cell line 3T3-A31.

Chemical Structure of Oncoretardine

The amino acid compositions of bBF and hBF were determined after hydrolysis with 6N HCl using an automatic amino acid analyzer. All common amino acids except cysteine were present in these proteins. The minimal molecular weights calculated from these data is approximately 9,900 in agreement with that established by SDS-PAGE.

No N-terminal amino acid was detected, even when several cycles of Edman degradation were performed, suggesting that the terminal amino groups of bBF and hBF are blocked. The sequences were determined as described in the Experimental section. The sequences of bBf and hBF are as follows:

| | | | | | Blocked N-terminal — | | | | | | | | | | | | |
|---|---|---|---|---|---|---|---|---|---|---|---|---|---|---|---|---|---|
| bBF | S | Q | A | E | F | D | K | A | A | E | E | V | K | H | L | K | T | K | P | A |
| hBF | S | Q | A | E | F | E | K | A | A | E | E | V | R | H | L | K | T | K | P | S |
| bBF | D | E | E | M | L | F | I | Y | S | H | Y | K | Q | A | T | V | G | D | I | N |
| hBF | D | E | E | M | L | F | I | Y | G | H | Y | K | Q | A | T | V | G | D | I | N |
| bBF | T | E | R | P | G | M | L | D | F | K | G | K | A | K | W | D | A | W | N | E |
| hBF | T | E | R | P | G | M | L | D | F | T | G | K | A | K | W | D | A | W | N | E |
| bBF | L | K | G | T | S | K | E | D | A | M | K | A | Y | I | D | K | V | E | E | L |
| hBF | L | K | G | T | S | K | E | D | A | M | K | A | Y | I | N | K | V | E | E | L |
| bBF | K | K | K | Y | G | I | — C-terminal | | | | | | | | | | | | | |
| hBF | K | K | K | Y | G | I | — C-terminal | | | | | | | | | | | | | |

Residues in the hBF amino acid sequences which differ from the bBF sequences are underlined.

A comparison of the amino acid sequences of hBF with the amino acid sequences of bBF indicates that human and bovine BF may differ from each other by only a few conservative substitutions. Five of six amino acid substitutions are compatible with a single base change at the DNA level. These results establish that human and bovine BFs are highly conserved structurally among different species.

Antibody Production Against bBF

Antisera to the purified factor from bovine brain were prepared in rats. Six-week-old Sprague-Dawley rats were primed subcutaneously at three sites along the back and intraperitoneally with a total of 20 μg of purified protein emulsified in Freund's complete adjuvant. Subsequent booster inoculations were given at two-week intervals using 10 μg of protein in Freund's incomplete adjuvant. Test bleeds were taken one week after each inoculation and screened for antibodies using the radioimmunoassay procedure outlines below. Antisera suitable for the assay were generally obtained after only two to three booster inoculations.

Radioimmunoassay

Purified bovine brain factor was radioiodinated with Chloramine-T to a specific activity of approximately $1 \times 10^{10}$ cpm/μg and stored at 4° C. in TNEN buffer (20 mM Tris-HCl, pH 7.4; 5 mM EDTA; 150 mM NaCl; 0.05% NP40; 0.1% BSA).

For the radioimmunoassay, the following reagents were successively added to polypropylene tubes (3 ml capacity): 10 μl of purified brain factor standard or sample, 10 μl of rat antiserum (diluted 1:30 in TNEN buffer) and 30 μl of $^{125}$I-labeled bovine brain factor ($\sim 5 \times 10^4$ cpm). After a 45 min incubation at room temperature, 50 μl of a 10% suspension of heat-inactivated formalin-fixed *S. aureus* was added and the mixture left for an additional 30 min. The immunoabsorbent was then centrifuged (15,000×g, 1 min) through a cushion of n-butylphathalate oil and the amount of radioactivity in the *S. aureus* pellet determined by γ-spectrometry.

Tissue to be assayed for RIA reactive material was processed as follows. Fresh or frozen tissue (approximately 1 g net weight) was added to 10 ml of cold homogenization buffer (20 mM Tris-HCl, pH 7.4; 5 mM EDTA; 150 mM NaCl; 0.2% NP40; 0.2 mM phenylmethylsulfonyl fluoride; 100 kallikrein inhibitor units of trasylol per ml) and homogenized by three 15 sec bursts in a Polytron tissue homogenizer. The extract was removed and cleaned of debris by centrifugation at 100,000×g. The supernatant was then heated to 95° C. for 5 min and centrifuged at low speed to remove precipitated protein. Serial 1:3 dilutions of the extract were made in TNEN buffer and used in the radioimmunoassay. A standard curve was included with each set of assays and the amount of immunological reactive material estimated by direct comparison.

DISTRIBUTION OF ONCORETARDINE

A radioimmunoassay (RIA) was developed for the detection of bBF using the polyclonal rat anti-bBF. Bovine brain, spleen and thymus were found to contain about 11.5, 7.6 and 6.8 μg equivalents of bBF per gram wet tissue, respectively. Human brain contained approximately 15.7 μg equivalent of bBF/g wet tissue. bBF was detected in all the regions of bovine brain. The highest concentration was seen in pons (21 μg/g wet tissue) and the lowest in corpus callosum (7.4 μg/g wet tissue) among all the bovine brain regions tested.

Identification and Characterization of a cDNA Clone for a Factor from Bovine Brain Poly (A+) RNA isolated from bovine tissue was used as a template for cDNA synthesis. First strand cDNA synthesis was performed using oligo (dT) and avian myeloblastosis virus (AMV) reverse transcriptase; the second strand was synthesized using *E. coli* RNase H, DNA polymerase I, and DNA ligase (NAD+). The double-stranded cDNA was made blunt-ended by $S_1$ nuclease digestion followed by a fill-in reaction with the large fragment of *E. coli* DNA polymerase I. Terminal deoxynucleotidyl transferase was used to enzymatically add approximately 15 deoxyguanine residues to the 3' ends of the cDNA. This G-tailed cDNA was then size-fractionated on an A-50 column to eliminate both cDNAs smaller than 500 base pairs, as well as unincorporated deoxyguanine residues. Pooled cDNA was then concentrated by ethanol precipitation in the presence of EcoRI digested λgt.10 DNA.

Ligation of the G-tailed cDNA to EcoRI cut λgt.10 was achieved via a novel method utilizing a single-stranded oligonucleotide linker which contained 12 deoxycytosines at the 3' end and a sequence (AATT) complementary to the single-stranded overhang of EcoRI-cleaved DNA at the 5' end. After in vitro packaging of the ligated DNA, recombinant phage were introduced into the *E. coli* strain C600rk⁻mk⁺ HF1, which undergoes cell lysis when infected by recombinant, but not wild type, phage. DNA from plaques were thereby screened in duplicate using a radiolabeled synthetic oligonucleotide, 17 nucleotides in length, whose sequence was predicted by 6 consecutive amino acids (KWDAWN) found in the bovine brain factor; due to codon ambiguity, MS1 was synthesized as a 32-fold degenerate pool of oligonucleotides. Screening with MS1 produced a positive clone which was plaque purified and shown to contain a 1.8 Kb insert. This insert was subcloned into the plasmid pEMB1 and is designated pBBF1. After restriction mapping of the insert, appropriate fragments were then further subcloned into strains of M13 and sequenced by the dideoxy method of Sanger and Coulsen.

The cDNA contained in pBBF1 included a DNA sequence approximately 300 base pairs from the 5' end of the insert which was nearly identical to a species of MS1. Furthermore, the nucleotide sequence of pBBF1 predicted an amino acid sequence similar, but not identical, to that determined for the sequenced bovine brain factor. That these two proteins are closely related is suggested by the striking conservation of amino acid sequence: by deleting three amino acids from the sequenced brain factor, it is possible to align the remaining amino acids with the sequence of pBBF1 so that 43% of the amino acids are conserved. In addition, a number of alterations comprise conservative substitutions.

The finding of pBBF1 demonstrates that the bovine brain factor is a member of a family of related genes which may encode proteins of similar biological activity. Finally, it should be noted that pBBF1 encodes a protein larger than the sequenced bovine brain factor since an open reading frame extends both upstream and downstream from the known terminal amino acids of the latter protein.

Amino acid sequence homology between the bovine brain factor and a protein predicted by the nucleotide sequence of pBBF1 is as follows. The nucleotide sequence of a cDNA clone (pBBF1) isolated from bovine brain as described in the text is presented in part, along with the single open reading frame predicted by that sequence. The known amino acid sequences of the bovine brain factor (bBF) and human brain factor (hBF) are also shown and homologous residues are boxed. The deletion of 3 amino acids from the bBF and hBF sequences in order to achieve optimal alignment is indicated.

```
pBBF1: GTTCACGAAACCCGGTTTGAGGCGGCTGTGAAGGTGATACAGAGCTTGCCGAAAAATGGTTCATTCCAG
        V  H  E  T  R  F  E  A  A  V  K  V  I  Q  S  L  P  K  N  G  S  F  Q
BBF:                                 S  Q  A  E  F  D  K  A  A  E  E  V  K  H  L  K  T  K pBBF1: CCAACAAATGAAATGATGCTCAAGTTCTATAGCTTCTATAAGCAGGCAACTGAAGGACCTTGTAAACTG
        P  T  N  E  M  L  K  F  Y  S  F  Y  K  Q  A  T  E  G  P  C  K  L
BBF:    P  A  D  E  E  M  L  F  I  Y  S  H  Y  K  Q  A  T  V  G  D  I  N  T pBBF1: TCAAAGCCTGGCTTCTGGGATCCTGTTGGAAGATACAAATGGGATGCGTGGAGTTCTTTGGGTGATATG
        S  K  P  G  F  W  D  P  V  G  R  Y  K  W  D  A  W  S  S  L  G  D  M
BBF:    E  R  P  G  M  L  D  F  K  G  K  A  K  W  D  A  W  N  E  L  K  G  T pBBF1: ACCAAAGAGAAGCCATGATTGCTTATGTTGAAGAAATGAAAAAGATTCTTGAAACTATGCCGATGACT
        T  K  E  E  A  M  I  A  Y  V  E  E  M  K  K  I  L  E  T  M  P  M  T
BBF:    S  K  E  D  A  M  K  A  Y  V  E  E  L  K  K  K  Y  G  I
                                                      I  D  K
```

It is evident from the above results that the subject compounds can be used in a wide variety of ways, both in vitro and in vivo. The subject polypeptides and antibodies can be used diagnostically for determining, intracellularly or extracellularly, in physiological fluids, e.g., blood, serum, plasma, urine, or cerebrospinal fluid, the presence of such polypeptides by recognized diagnostic assays, for determination of the amount of the polypeptide formed by cells in tissue. Also, the subject compounds can be used for the detection of receptors for the polypeptides. In addition, the subject compounds can be used for modulating the rate of growth of tumor cells, both in the presence and absence of normal cells. Thus, the subject compounds can be used in conjunction with other additives for removing tumor cells from a mixture of normal and tumor cells, such as in bone marrow, tumors, e.g., melanomas, sarcomas, or carcinomas, for surgical or post-surgical treatments, or the like.

Although the foregoing invention has been described in some detail by way of illustration and example for purposes of clarity of understanding, it will be obvious that certain changes and modifications may be practiced within the scope of the appended claims.

What is claimed is:

1. A method for retarding the growth of neoplastic cells which comprises:
   applying to neoplastic cells a growth retarding amount of a polypeptide of at least about 15 amino acids having a sequence the same as a sequence of a neoplastic cell retarding polypeptide found in mammalian brain, with the proviso that there are not more than two amino acid changes and an insertion or deletion of not more than three amino acids.

2. A method for retarding the growth of neoplastic cells which comprises:
   applying to neoplastic cells a growth retarding amount of a polypeptide of at least about 15 amino acids having a sequence which includes at least one of the following:

Yaa$^e$aa$^a$YKQATaa$^b$      a.

KWDAW      b.

AMaa$^c$AY(X)$_x$VEE      c.

TKPaa$^d$aa$^p$EEMLFIYaa$^e$HYK      d.

wherein:
   aa$^a$ is an aromatic amino acid;
   aa$^b$ and aa$^c$ are any amino acid;
   aa$^d$ and aa$^e$ are aliphatic neutral amino acids; and
   aa$^p$ is an aliphatic amino acid.

3. A method according to claim 2, wherein said polypeptide includes at least one of the following sequences:

TAKPaa$^d$DEEMLFIYaa$^e$HYKQATaa$^f$G      a.

KWDAWaa$^g$aa$^h$Laa$^i$aa$^j$aa$^k$aa$^l$K-
      Eaa$^m$AMaa$^n$AY(X')$_x$VEEaa$^o$KK      b.

wherein:
   aa$^f$ is an aliphatic amino acid, or from 4 to 6 carbon atoms;
   aa$^g$ is an aliphatic neutral molar amino acid of from 3 to 5 carbon atoms;
   aa$^h$ is an aliphatic amino acid of from 3 to 5 carbon atoms, which is neutral or acidic;
   aa$^i$ is an aliphatic amino acid of from about 2 to 6 carbon atoms;
   aa$^j$ is an aliphatic amino acid of from 2 to 5 carbon atoms;
   aa$^k$ is an aliphatic neutral polar amino acid of from 3 to 5 carbon atoms;
   aa$^l$ is an aliphatic neutral polar amino acid of from 3 to 4 carbon atoms;
   aa$^m$ is an aliphatic acidic amino acid of from 4 to 5 carbon atoms;
   aa$^n$ is an aliphatic neutral or basic amino acid of from 3 to 6 carbon atoms;
   X' is of from 1 to 3 amino acids of from 4 to 6 carbon atoms;
   x is 0 or 1; and
   aa$^o$ is an aliphatic neutral amino acid of from 4 to 6 carbon atoms.

4. A method according to claim 1, wherein said polypeptide is derived from mammalian brain and elutes in the fraction from about 30% to 50% acetonitrile in 0.1% aqueous trifluoroacetic acid on a reverse phase HPLC column and is of from about 8 to 18 kDal.

5. A method according to claim 4, wherein said polypeptide includes the following amino acid sequence:

```
F—E—A—A—V—K—V—I —Q—S—L—P—K—N—G—
S  Q    E  F  D  K  A  A  E  E  V  K  H  L
              E                          R

—S —F—Q—P—T—N—E—M—M—L—K—F—Y—S —
 K  T  K     A  D  E        F  I    S
             S                       G

—F—Y—K—Q—A—T—E—G—P—C—K—L—S—K—
 H              V     D  I  N  T  E  R

—P—G—F —W—D—P—V—G—R—Y—K—W—D—A—
     M  L     F  K     K  A
              T

—W—S—S—L—G—D—M—T—K—E—E—A—M—I —
    N  E    K  G  T  S     D     M  K

A—Y—*—*—*—V—E—E—M—K—K—I —L—E—T
    I  D  K        L        K  Y  G  I
       N
``` where a plurality of amino acids at a site indicates each amino acid may be employed at that site and an asterisk (*) intends a bond may be employed at that site.

6. A method according to claim 5, wherein said polypeptide includes the following amino acid sequence:

V-H-E-T-R-F-E-A-A-V-K-V-I-Q-S-L-P-K-N

G-S-F-Q-P-T-N-E-M-M-L-K-F-Y-S-F-Y-K-Q

A-T-E-G-P-C-K-L-S-K-P-G-F-W-D-P-V-G-R

Y-K-W-D-A-W-S-S-L-G-D-M-T-K-E-E-A-M-I

A-Y-V-E-E-M-K-K-I-L-E-T-M-P-M-T

7. A method according to claim 5, wherein said polypeptide includes the following amino acid sequence:

S—Q—A—E—F—D—K—A—A—E—E—V—K—H—L—
                         20
—K—T—K—P—A—D—E—E—M—L—F—I—Y—S—
                         40
—H—Y—K—Q—A—T—V—G—D—I—N—T—E—R—

—P—G—M—L—D—F—K—G—K—A—K—W—D—A—
                         60
—W—N—E—L—K—G—T—S—K—E—D—A—M—K—
                         80
—A—Y—I—D—K—V—E—E—L—K—K—K—Y—G—I

8. A method according to claim 5, wherein said polypeptide includes the following amino acid sequence:

S—Q—A—E—F—E—K—A—A—E—E—V—R—H—L—
                         20
—K—T—K—P—S—D—E—E—M—L—F—I—Y—G—
                         40
—H—Y—K—Q—A—T—V—G—D—I—N—T—E—R—

—P—G—M—L—D—F—T—G—K—A—K—W—D—A—
                         60
—W—N—E—L—K—G—T—S—K—E—D—A—M—K—
                         80
—A—Y—I—N—K—V—E—E—L—K—K—K—Y—G—I

9. A composition of matter comprising a polypeptide sequence of at least 15 amino acids and not more than 125 amino acids having at least one epitopic site cross reactive with a polypeptide found in mammalian brain capable of retarding neoplastic cell growth in vitro, said polypeptide including at least one of the following peptide sequences:

| | |
|---|---|
| Yaa$^e$aa$^a$YKQATaa$^b$ | a. |
| KWDAW | b. |
| AMaa$^c$AY(X)$_x$VEE | c. |
| TKPaa$^d$aa$^p$EEMLFIYaa$^e$HYK | d. | wherein:
aa$^a$ is an aromatic amino acid;
aa$^b$ and aa$^c$ are any amino acids;
aa$^d$ and aa$^e$ are aliphatic neutral amino acids; and
aa$^p$ is an aliphatic amino acid.

10. A composition according to claim 9, wherein said composition includes at least one of the following sequences:

| | |
|---|---|
| TKPaa$^d$DEEMLFIYaa$^e$HYKQATaa$^f$G | a. |
| KWDAWaa$^g$aa$^h$Laa$^i$aa$^j$aa$^k$aa$^l$K-Eaa$^m$AMaa$^n$AY(X')$_x$VEEaa$^o$KK | b. | wherein:
aa$^f$ is an aliphatic amino acid, or from 4 to 6 carbon atoms;
aa$^g$ is an aliphatic neutral polar amino amino acid of from 3 to 5 carbon atoms;
aa$^h$ is an aliphatic amino acid of from 3 to 5 carbon atoms, which is neutral or acidic;
aa$^i$ is an aliphatic amino acid of from about 2 to 6 carbon atoms;
aa$^j$ is an aliphatic amino acid of from 2 to 5 carbon atoms;
aa$^k$ is an aliphatic neutral polar amino acid of from 3 to 5 carbon atoms;
aa$^l$ is an aliphatic neutral polar amino acid of from 3 to 4 carbon atoms;
aa$^m$ is an aliphatic acidic amino acid of from 4 to 5 carbon atoms;
aa$^n$ is an aliphatic neutral or basic amino acid of from 3 to 6 carbon atoms;
X' is of from 1 to 3 amino acids of from 4 to 6 carbon atoms;
x is 0 or 1; and
aa$^o$ is an aliphatic neutral amino acid of from 4 to 6 carbon atoms.

11. A composition according to claim 9, wherein said polypeptide is characterized by eluting in the 30% to 50% acetonitrile fraction in aqueous 0.1M trifluoroacetic acid, is of from about 8,000 to 18,000 molecular weight, and is found in mammalian brains.

12. A composition of matter according to claim 9, said polypeptide sequence including the following sequence:

```
F—E—A—A—V—K—V—I —Q—S—L—P—K—N—G—
S  Q    E  F  D  K  A  A  E  E  V  K  H  L
              E                          R

—S —F—Q—P—T—N—E—M—M—L—K—F—Y—S —
 K  T  K     A  D  E        F  I    S
             S                       G
```

-continued

```
—F—Y—K—Q—A—T—E—G—P—C—K—L—S—K—
 H               V     D   I N T E R

—P—G—F—W—D—P—V—G—R—Y—K—W—D—A—
     M L     F K     K A
             T

—W—S—L—G—D—M—T—K—E—E—A—M—I—
 N E     K G T S     D       K

A—Y—*—*—*—V—E—E—M—K—K—I—L—E—T
   I D K         L       K Y G I
     N
``` where a plurality of amino acids at a site indicates each amino acid may be employed at that site and an asterisk (*) intends a bond may be employed at that site.

13. A composition of matter according to claim 12, said polypeptide sequence including the following amino acid sequence:

V-H-E-T-R-F-E-A-A-V-K-V-I-Q-S-L-P-K-N

G-S-F-Q-P-T-N-E-M-M-L-K-F-Y-S-F-Y-K-Q

A-T-E-G-P-C-K-L-S-K-P-G-F-W-D-P-V-G-R

Y-K-W-D-A-W-S-S-L-G-D-M-T-K-E-E-A-M-I

A-Y-V-E-E-M-K-K-I-L-E-T-M-P-M-T

14. A composition of matter according to claim 12 including the following amino acid sequence:

```
S—Q—A—E—F—D—K—A—A—E—E—V—K—H—L—
              20
—K—T—K—P—A—D—E—E—M—L—F—I—Y—S—
                    40
—H—Y—K—Q—A—T—V—G—D—I—N—T—E—R—
—P—G—M—L—D—F—K—G—K—A—K—W—D—A—
              60
—W—N—E—L—K—G—T—S—K—E—D—A—M—K—
                    80
—A—Y—I—D—K—V—E—E—L—K—K—K—Y—G—I
```

15. A composition of matter according to claim 12 including the following amino acid sequence:

```
S—Q—A—E—F—E—K—A—A—E—E—V—R—H—L—
              20
—K—T—K—P—S—D—E—E—M—L—F—I—Y—G—
                    40
—H—Y—K—Q—A—T—V—G—D—I—N—T—E—R—
—P—G—M—L—D—F—T—G—K—A—K—W—D—A—
              60
—W—N—E—L—K—G—T—S—K—E—D—A—M—K—
                    80
—A—Y—I—N—K—V—E—E—L—K—K—K—Y—G—I
```

16. Antibodies capable of binding to and prepared in response to the composition or immunogenic fragment thereof, said composition comprising a polypeptide sequence of at least 15 amino acids and not more than 125 amino acids having at least one epitopic site cross reactive with a polypeptide found in mammalian brain capable of retarding neopastic cell growth in vitro, said polypeptide including at least one of the following peptide sequences:

| | |
|---|---|
| Yaa$^e$aa$^a$YKQATaa$^b$ | a. |
| KWDAW | b. |
| AMaa$^c$AY(X)$_x$VEE | c. |
| TKPaa$^d$aa$^p$EEMLFIYaa$^e$HYK | d. | wherein:
aa$^a$ is an aromatic amino acid;
aa$^b$ and aa$^c$ are any amino acid;
aa$^d$ and aa$^e$ are aliphatic neutral amino acids; and
aa$^p$ is an aliphatic amino acid.

17. Antibodies according to claim 16, which are monoclonal antibodies.

18. A method for detecting the presence of a polypeptide found in mammalian brains of from about 8,000 to 18,000 molecular weight and capable of preferentially retarding neoplastic cell growth as compared to normal growth, which comprises:

combining antibodies capable of binding to and prepared in response to a polypeptide comprising a polypeptide sequence of at least 15 amino acids and not more than 125 amino acids having at least one epitopic site cross-reactive with a polypeptide found in mammalian brain capable of retarding neoplastic cell growth in vitro, said polypeptide including at least one of the following peptide sequences:

| | |
|---|---|
| Yaa$^e$aa$^a$YKQATaa$^b$ | a. |
| KWDAW | b. |
| AMaa$^c$AY(X)$_x$VEE | c. |
| TKPaa$^d$aa$^p$EEMLFIYaa$^e$HYK | d. | wherein
aa$^a$ is an aromatic amino acid:
aa$^b$ and aa$^c$ are any amino acids;
aa$^d$ and aa$^e$ are aliphatic neutral amino acids; and
aa$^p$ is an aliphatic amino acid with a sample suspected of containing said polypeptide and determining the presence of complex formation with said antibodies.

* * * * *